US006602230B1

(12) United States Patent
Fisher et al.

(10) Patent No.: US 6,602,230 B1
(45) Date of Patent: Aug. 5, 2003

(54) PORTABLE CONTAINER FOR EMESIS

(76) Inventors: Jeffrey J. Fisher, 4780 Oak Dr., Moose Lake, MN (US) 55767; Mary J. Krohn, 4780 Oak Dr., Moose Lake, MN (US) 55767

( * ) Notice: Subject to any disclaimer, the term of this patent is extended or adjusted under 35 U.S.C. 154(b) by 0 days.

(21) Appl. No.: 09/768,108

(22) Filed: Jan. 23, 2001

Related U.S. Application Data

(60) Provisional application No. 60/178,267, filed on Jan. 27, 2000.

(51) Int. Cl.[7] .................................... A61M 1/00
(52) U.S. Cl. .................................... 604/317
(58) Field of Search .................................... 604/317–326, 604/346–354

(56) References Cited

U.S. PATENT DOCUMENTS

| | | | | |
|---|---|---|---|---|
| D37,300 | S | | 1/1905 | Meinecke |
| 805,312 | A | | 11/1905 | Meinecke |
| 1,714,572 | A | | 5/1929 | Sears |
| D91,211 | S | | 12/1933 | O'Mahony |
| D135,195 | S | | 3/1943 | Bal et al. |
| 2,687,534 | A | | 8/1954 | Johnson |
| D212,516 | S | | 10/1968 | Beich |
| D213,408 | S | | 2/1969 | Brodsky et al. |
| 3,635,091 | A | * | 1/1972 | Linzer et al. ............... 600/574 |
| 3,716,871 | A | | 2/1973 | Borse |
| 3,727,244 | A | | 4/1973 | Collins |
| D244,403 | S | | 5/1977 | DeAngelis |
| 4,026,433 | A | | 5/1977 | Crippa |
| D248,168 | S | | 6/1978 | Kelly |
| 4,270,231 | A | | 6/1981 | Zint |
| D273,133 | S | | 3/1984 | Babic et al. |
| 4,665,571 | A | | 5/1987 | Muccione |
| 4,696,067 | A | | 9/1987 | Woodward |
| 4,769,858 | A | | 9/1988 | Gamm et al. |
| D304,373 | S | | 10/1989 | Floyd |
| 5,282,599 | A | | 2/1994 | Arpaia et al. |
| 5,342,330 | A | | 8/1994 | Kane et al. |
| 5,387,205 | A | | 2/1995 | Cummins |
| 5,406,651 | A | | 4/1995 | Nogay |
| 5,425,468 | A | | 6/1995 | Birkel et al. |
| 5,599,332 | A | | 2/1997 | Cashel |
| D389,240 | S | | 1/1998 | Corona |
| 5,797,147 | A | | 8/1998 | Young et al. |
| 5,839,123 | A | * | 11/1998 | Dunham, Sr. ................ 4/144.1 |
| 6,021,529 | A | | 2/2000 | Abbato |
| 6,026,519 | A | | 2/2000 | Kaluza |
| 6,210,382 | B1 | * | 4/2001 | Hogg ......................... 600/573 |

* cited by examiner

*Primary Examiner*—Weilun Lo
*Assistant Examiner*—C. Lynne Anderson

(57) ABSTRACT

A container for receiving and holding emesis has an inclined body providing an inclined chamber for storing emesis. A curved funnel has a small end joined to the body and a large inclined end surrounding an inclined mouth. A handle is joined to the funnel adjacent the lower portion of the large inclined end. A cover is snapped on the large inclined end of the funnel to contain emesis and odor within the container.

12 Claims, 4 Drawing Sheets

PORTABLE CONTAINER FOR EMESIS

This application claims the benefit of Provisional Application No. 60/178,267, filed Jan. 27, 2000.

FIELD OF THE INVENTION

The invention relates to a container used in the health care filed for receiving and holding human body fluids. The container is a portable one-piece receptacle specifically useable to receive and accommodate involuntary emesis and emesis induced with an emetic medicine or agent. The container is in compliance with body fluid containment standards including the safe and efficient collecting and containment of emesis.

BACKGROUND OF THE INVENTION

Disease control standards require that emesis be contained to prevent risk of external contamination of caregivers, person and objects. Emesis at times contain blood, lung fluids, and stomach contents and present a risk of contamination by HIV, Hepatitis B, and non-blood borne pathogens. Numerous devices have been disclosed for handling body fluids, including urine and emesis. An example of a portable receptacle for receiving and containing emesis is disclosed by K. A. Cashel in U.S. Pat. No. 5,599,332. This receptacle has a main body having an emesis containment chamber and a neck joined to the body. A mouthpiece having an open end shaped to abut a person's face around the mouth fits into the neck to direct emesis into the neck and chamber of the body. The neck includes a baffling device to minimize back flow or splashing or spillage of emesis. Handles on opposite sides of the body are used by the person emitting emesis to facilitate positioning of the mouthpiece adjacent the person's mouth. The present invention is an improvement in emesis containers that is splash and spill effective without baffling devices, convenient, cost efficient and disposable.

SUMMARY OF THE INVENTION

The invention is a portable container or receptacle for use in accepting and containing emesis and sputum. The container has a tubular body joined to a funnel with a handle secured to the funnel. The body has an upward inclined side wall and bottom wall providing a chamber for accommodating emesis. The bottom wall is flat to permit the container to stand upright at an incline on a flat surface. The funnel has a mouth open at an angle of about 45 degrees relative to the vertical axis of the body. The mouth has an area larger than the cross-sectional area of the chamber of the body. The funnel has a truncated cone shape that extends at an angle of about 45 degrees relative to the body to locate the mouth toward the person using the container. The curvature of the cone-shaped funnel and angle of the funnel combined with the inclined body minimizes back flow, spilling and splashing of emesis out of the containment chamber of the body. The handle is an elongated generally cylindrical member extended downwardly from the lower portion of the funnel which is used to stabilize and assist holding of the container by a person or caregiver. A flexible neck joins the upper end of the handle to a semi-hemispherical section of the funnel. The neck allows the handle to be laterally moved relative to the body. The container is a one-piece plastic structure. The open peripheral end of the funnel has an outwardly directed annular rib. A cover having an annular lip with an internal circular groove snaps on the rib to close the opening of the mouth of the funnel. The handle is spaced from the body to allow a person's hand to firmly grip the handle and retain the container in a desired position. The container accommodates a volume greater than 1000 milliliters and is large enough to handle the contents of a person's full stomach.

DESCRIPTION OF THE INVENTION

The container of the invention, indicated generally 10 in FIGS. 1 to 4 and 9, is a portable collector and retainer of body liquids and semi-solids, known as emesis. Container 10 used as an aid to body fluid containment has a capacity greater than 1000 milliliters to accommodate fluids from a full human stomach. The body fluid containment function of the container complies with the OSHA blood borne pathogen standard, 29 CFR Part 1910.1030.

Figure 9:
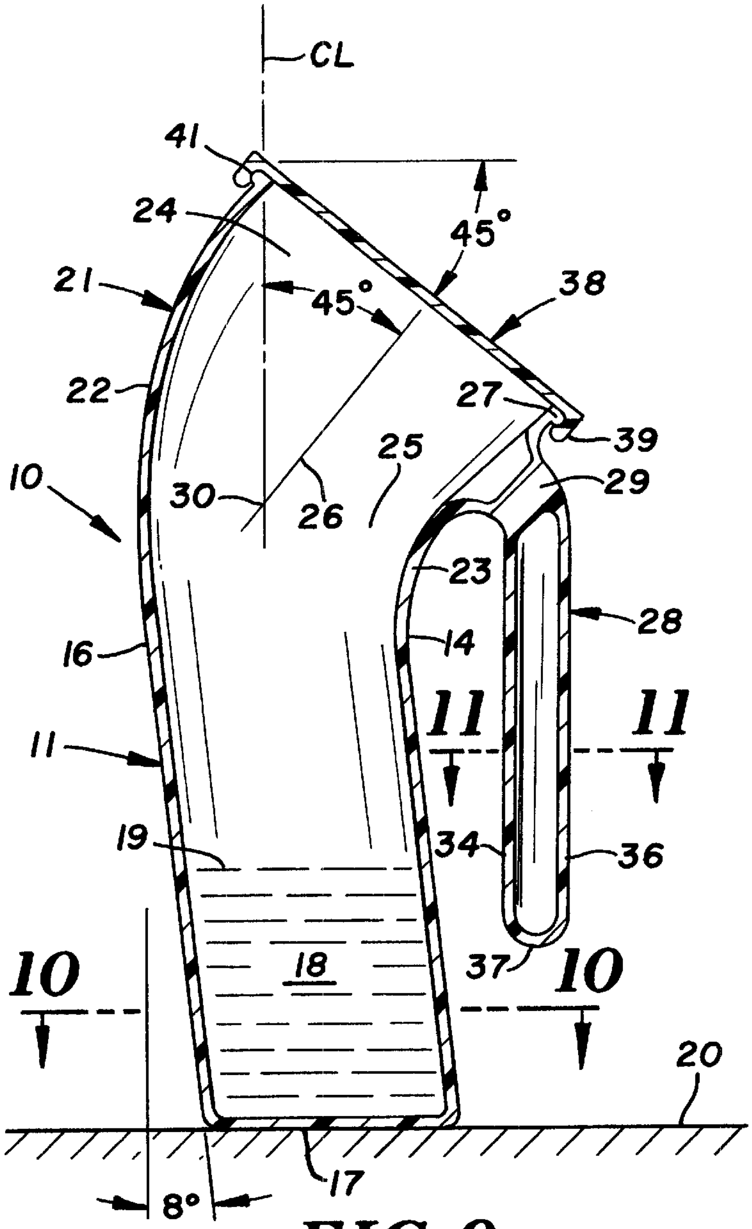
FIG. 9 is an enlarged sectional view taken along the line 9—9 of FIG. 9.
Figure 10:
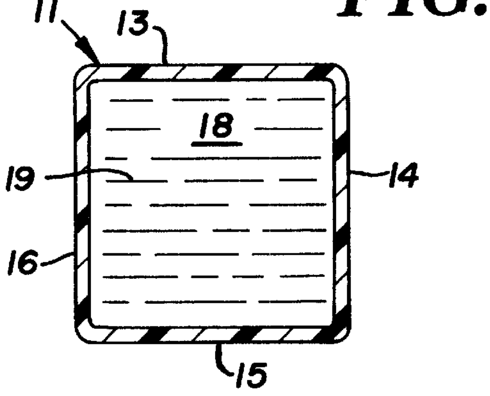
FIG. 10 is a sectional view taken along line 10—10 of FIG. 9.

Container 10 has an upright tubular body 11 joined to a conical-shaped funnel 21 for receiving body fluids and directing the body fluids into a collection chamber 18 surrounded by body 11. Body 11 has flat upright side walls 13, 14, 15 and 16 joined to a flat bottom wall 17. Side wall 14 is a proximal upright inclined wall. Side wall 6 is a distal upright inclined wall. As shown in FIG. 9, proximal and distal side walls 14 and 16 extend upwardly at an angle of 8 degrees relative to a vertical line or axis CL when the bottom wall 17 rests on a flat horizontal surface 20. The incline of walls 14 and 16 can vary between 5 to 12 degrees relative to vertical line CL. As shown in FIG. 10, body 11 has a square cross section with walls 13, 14, 15 and 16 having the same thickness and width. adjacent walls are joined with rounded corners. The lower edges of walls 13, 14, 15 and 16 are joined to the outer edges of bottom wall 17 to form chamber 18 for holding body fluids or emesis 19. Funnel 21 is a curved cone having an outer or distal arcuate wall 22 joined to side wall 16 and an inner or proximal arcuate wall 23 joined to side wall 16. Wall 22 has a radius of curvature larger than the radius of curvature of wall 23. Wall 22 curves upwardly to the center line CL and top edge of an inclined mouth 24. Mouth 24 is a circular opening providing an entrance to the throat passage 25 open to chamber 18. Mouth 24 inclines downwardly in a proximal direction toward handle 28. The center line 26 of mouth 24 and funnel 21 is located 45 degrees from center line CL. This angle can vary from 35 to 55 degrees from center line CL. Center line 26 and vertical line CL intersect at 30 located in throat passage 25. A circular rib 27 joined to the outer peripheral edge of funnel 21 reinforces the outer end of funnel 21 and provides a holding ring for accommodating a cover 38.

Figure 11:
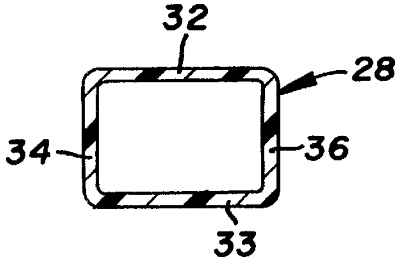
FIG. 11 is an enlarged sectional view taken along line 11—11 of FIG. 10.

As shown in FIGS. 1, 2, 3, and 9, an upright linear handle, indicated generally at 28, is connected to proximal wall 23 with a flat neck 29. Wall 23 has a semi-hemispherical extension 31 joined to neck 29 which locates handle 28 away from side wall 14. Neck 29 is a solid vertically orientated member of flexible plastic that allows handle 28 to be moved laterally relative to body 11 and funnel 21. Extension 31 reinforces curved proximal wall 23 and provides a strong support for neck 29 and handle 28. As shown in FIG. 11, handle 28 has a generally rectangular cross-section with flat sides 32 and 33 and flat ends 34 and 36. The lower end 37 of handle 28 is hollow to reduce the weight of the handle and allow for limited flexing by the hand of the user. Handle 28 is shorter than the vertical length body 11 and does not contact support 20 when bottom wall 17 rests on support 20, as seen in FIG. 9.

The open end or mouth 24 of funnel 21 is closed with a circular cover 38. Cover 38 is a circular disk having a circular outer peripheral flange 39. The inner surface of flange 39 has a circular groove 41. In use flange 39 snaps over rib 27 to locate rib 27 in groove 41 to seal cover 38 on funnel 21 and contain fluids 19 and odors to chamber 18 and the enclosed space of funnel 21.

Figure 1:
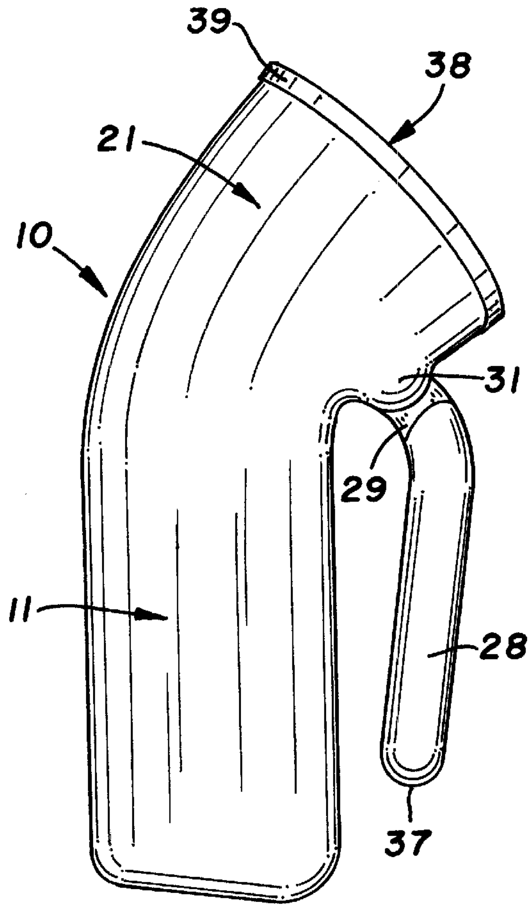
FIG. 1 is a perspective view of the portable emesis container of the invention.
Figure 2:
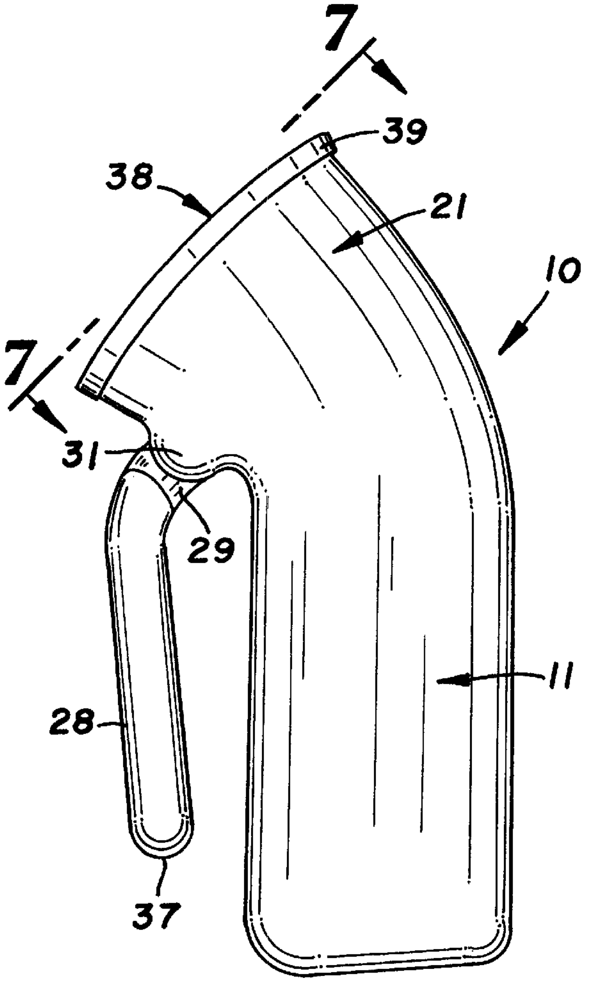
FIG. 2 is a side elevational view thereof; the opposite side being a mirror image thereof.
Figure 3:
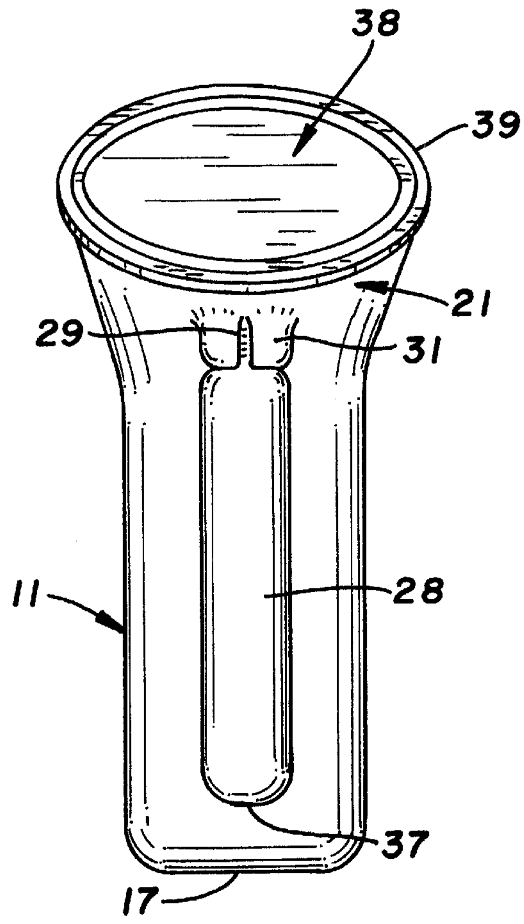
FIG. 3 is a proximate elevational view thereof.
Figure 4:
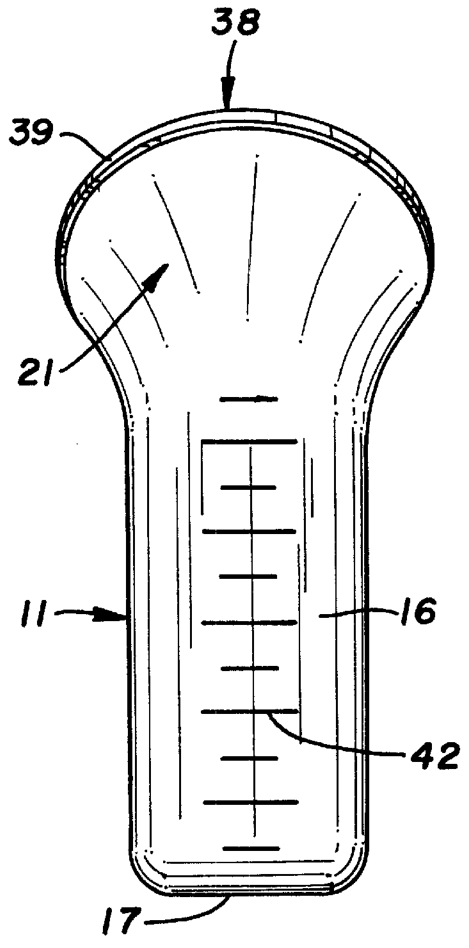
FIG. 4 is a distal elevational view thereof.
Figure 5:
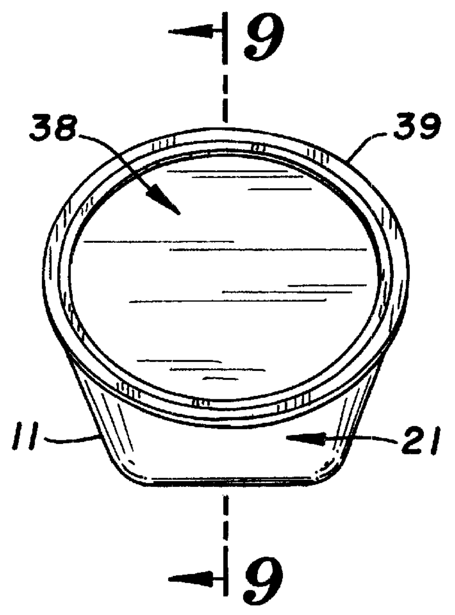
FIG. 5 is a top plan view thereof.
Figure 6:
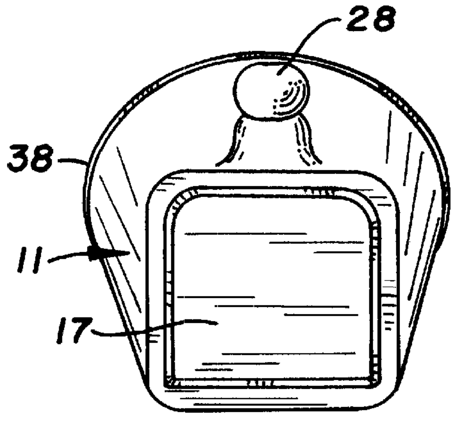
FIG. 6 is a bottom plan view thereof.
Figure 7:
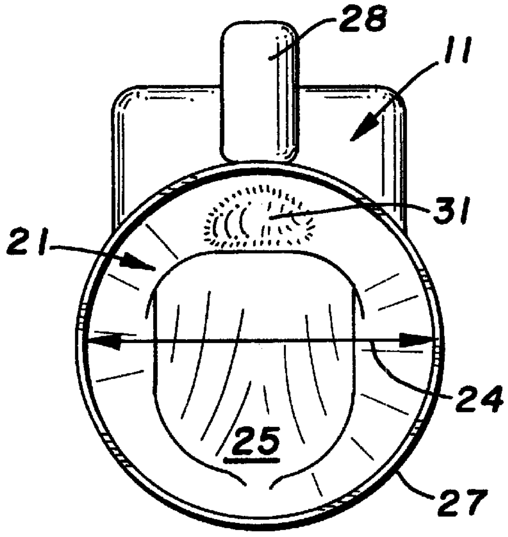
FIG. 7 is a view taken along the line 7—7 shown in FIG. 2.
Figure 8:
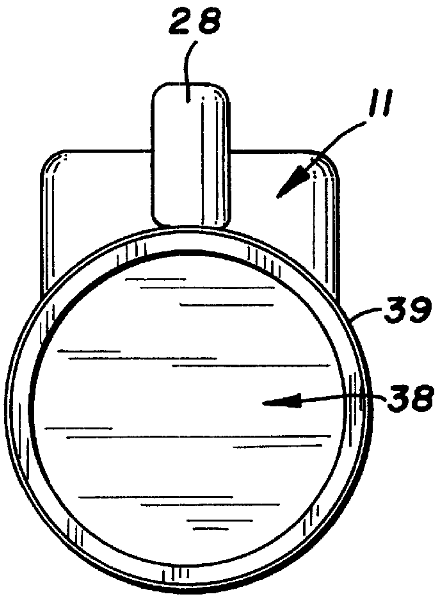
FIG. 8 is a top plan view of the cover for the container.

As shown in FIG. 4, distal wall 16 of body 11 has a vertical scale or measurement markings 42 used to visually determine the total volume of liquid 19 in chamber 18. Wall 16 is a semi-transparent plastic, such as polyethylene, which allows for visual observation of the level of liquid in chamber 18. Scale 42 can be located on either side wall 13 or 15.

The entire container 10 comprising body 11, funnel 21 and handle 28 is a one-piece molded plastic. The plastic is semi-transparent polyethylene. Other plastics can be used to make container 10. The plastic is compatible with emesis and does not crack or leak liquids or gases.

An example of the emesis container and cover has a one-piece plastic body 11, funnel 21 and handle 28. The plastic is polyethylene. Other types of plastic can be used to make the one-piece container 10. The body 11 square cross-section with each side having a dimension of 8 cm and a height of 16 cm. The entire body 11 inclines in distal upward direction 8 degrees relative to the vertical line. The funnel 21 is a truncated cone with a distal curved wall 22 having a curved length of 6 cm and a proximal curved wall 23 having a curved length of 3 cm. The open end or mouth 24 has a diameter of 12 cm and is inclined upwardly and outwardly at an angle of 45 degrees relative to the vertical line or axis of container 10. The cross-sectional area of mouth 24 is greater than the cross-sectional area of body 11. Mouth 24 has a cross-sectional area of 120 square cm. Body 11 has a cross-sectional area of 64 square cm. Handle 28 has a length of 13 cm with end 37 space about 3 cm above the plane of bottom wall 17. The end 37 of handle 28 does not engage the support 20 when bottom wall 17 rests on support 20.

In use, cover 38 is removed from funnel 21 by releasing flange 39 from rib 27 to open mouth 24. Handle 28 and body 11 are used to stabilize the container during usage. The person or caregiver grips handle 28 with one hand and holds body 11 with the other hand and moves mouth 24 adjacent the front of the person's face. Container 10 can be held with one hand gripping handle 28. Emesis is directed into funnel 21 through mouth 24 into throat passage 25. The concave curvature of the inside surface of distal wall 22 angularly deflects emesis into body chamber 18. The emesis being angularly directed in the inclined chamber 18 minimizes splashing and scattering of emesis back into throat 25 and funnel 21. The smaller area of throat relative to the converging area of the cone-shaped funnel also inhibits back splashing of emesis into funnel 21. The volume graduations 42, shown in FIG. 4, permit easy measurement of emesis in chamber 18. When emesis discharge is completed, cover 38 is snapped on rib 27 to close mouth 24 to confine emesis 19 and odors to chamber 18 and enclosed space of funnel 21. Container 10 is portable and is disposed of in a bio-compatible manner. Container 10 can be emptied, cleaned, sterilized and reused.

A preferred embodiment of the emesis container and cover has been disclosed in the specification and drawings. Changes in the shape, arrangement of parts of the container, and materials used to make the container and cover may be made by one skilled in the art without departing from the invention.

What is claimed is:

1. A portable container for receiving and holding human emesis comprising: a body having upright side walls and a flat bottom wall joined to the side walls surrounding a chamber for holding emesis, said side walls having proximal and distal walls extended upwardly at an angle of about 8 degrees relative to a vertical center line extended through the chamber of the body, a curved cone-shaped funnel joined to the upright side walls, said funnel having arcuate walls curved upwardly in the direction of the proximal wall, an outer circular end surrounding a circular opening, and a throat section joined to the side walls open to the chamber, said throat section being smaller than the outer circular end, said funnel having an axis extended at an angle of about 45 degrees relative to said vertical center line, said axis intersecting the vertical center line in the area surrounded by the throat section of the funnel, handle means secured to the funnel providing a grip for the hand of a user of the container, said handle means extended downwardly below the funnel adjacent the proximal wall of the body, said handle means having a lower end located at an elevation above the plane of the bottom wall, and cover means releasably mounted on the outer circular end of the funnel for closing the circular opening of the funnel and confining emesis and odors within the container.

2. The container of claim 1 wherein: the side walls of the body have a square cross-sectional shape.

3. The container of claim 1 wherein: said circular opening has a cross-sectional area greater than the cross-sectional area of the chamber of the body.

4. The container of claim 1 wherein: said funnel has an outwardly directed semi-hemispherical section, and a generally flat vertically orientated neck joined to the handle means and semi-hemispherical section to connect the handle means to the funnel.

5. The container of claim 1 wherein: said outer circular end of the funnel has an outwardly projected circular rib, said cover means having a circular flange having an internal circular groove, said flange located around said outer circular end with the rib located in the groove when the cover means is mounted on the funnel.

6. The container of claim 1 wherein: the body, the funnel, and the handle means are a one-piece plastic container.

7. A portable container for receiving and holding human body fluids comprising: a body having upwardly inclined side walls and a bottom wall joined to the outer walls surrounding a chamber for holding body fluids, said chamber having a cross-sectional area and a vertical center line, an outwardly curved cone-shaped funnel having a large outer end surrounding a circular opening and an inner end, said circular opening having a cross-sectional area greater than the cross-sectional area of the chamber of the body, said inner end being smaller in size than the outer end and joined to the side walls of the body, said funnel having curved walls extended upwardly and outwardly from the inner end to the outer end thereof, said funnel having an axis extended at an angle of between 35 to 65 degrees relative to the vertical center line extended through the chamber of the body, said axis of the funnel intersecting the vertical center line of the chamber in the area surrounded by the inner end of the funnel, handle means secured to the funnel providing a grip for the hand of a user of the container, said handle means extended downwardly from the funnel adjacent one of the side walls of the body, and a cover releasably mounted on the outer end of the funnel closing the circular opening to confine the body fluids in the chamber.

8. The container of claim 7 wherein: the side walls of the body have a square cross-sectional shape.

9. The container of claim 7 wherein: said funnel has an outwardly directed semi-hemispherical section, and a generally flat vertically orientated neck joined to the handle means and semi-hemispherical section to connect the handle means to the funnel.

10. The container of claim 7 wherein: said outer end of the funnel has an outwardly projected circular rib, said cover having a circular flange having an internal groove, said flange located around said outer end with the rib located in the groove when the cover is mounted on the funnel.

11. The container of claim 7 wherein: the body, the funnel, and the handle means are a one-piece plastic structure.

12. The container of claim 7 wherein: the handle means has a lower end located at an elevation above the plane of the bottom wall.

* * * * *